United States Patent
Smith et al.

(10) Patent No.: US 10,734,110 B2
(45) Date of Patent: Aug. 4, 2020

(54) CAREGIVER LOCATING TAG HAVING ADVANCED FUNCTIONALITY

(71) Applicant: Hill-Rom Services, Inc., Batesville, IN (US)

(72) Inventors: Bradley T. Smith, Raleigh, NC (US); Andrew S. Robinson, Durham, NC (US); Steven D. Baker, Beaverton, OR (US); Pamela Wells, Hixson, TN (US); John S. Schroder, Apex, NC (US); Kiana M. Dezelon, Batesville, IN (US); Laura A. Hassey, Raleigh, NC (US); Thomas A. Myers, Syracuse, NY (US); Eric D. Agdeppa, Cincinnati, OH (US); Varad N. Srivastava, Skaneateles, NY (US)

(73) Assignee: Hill-Rom Services, Inc., Batesville, IN (US)

(*) Notice: Subject to any disclaimer, the term of this patent is extended or adjusted under 35 U.S.C. 154(b) by 0 days.

(21) Appl. No.: 16/678,568

(22) Filed: Nov. 8, 2019

(65) Prior Publication Data
US 2020/0185087 A1    Jun. 11, 2020

Related U.S. Application Data

(60) Provisional application No. 62/775,468, filed on Dec. 5, 2018.

(51) Int. Cl.
| | | |
|---|---|---|
| E21B 47/00 | (2012.01) | |
| G16H 40/20 | (2018.01) | |
| G08B 21/02 | (2006.01) | |
| H04W 4/029 | (2018.01) | |
| G08B 3/10 | (2006.01) | |
| G08B 27/00 | (2006.01) | |
| G08B 5/22 | (2006.01) | |

(52) U.S. Cl.
CPC ............ *G16H 40/20* (2018.01); *G08B 3/1016* (2013.01); *G08B 5/223* (2013.01); *G08B 21/02* (2013.01); *G08B 27/00* (2013.01); *H04W 4/029* (2018.02)

(58) Field of Classification Search
CPC ...... G16H 40/20; H04W 4/029; G08B 3/1016; G08B 5/223; G08B 21/02; G08B 27/00
See application file for complete search history.

(56) References Cited

U.S. PATENT DOCUMENTS

| | | |
|---|---|---|
| 3,439,320 A | 4/1969 | Ward |
| 3,739,329 A | 6/1973 | Lester |
| (Continued) | | |

FOREIGN PATENT DOCUMENTS

| | | |
|---|---|---|
| GB | 2 193 359 A | 2/1988 |
| GB | 2 230 365 A | 10/1990 |
| (Continued) | | |

*Primary Examiner* — Munear T Akki
(74) *Attorney, Agent, or Firm* — Barnes & Thornburg LLP (57) ABSTRACT

A caregiver badge system includes a caregiver badge configured to be worn by a caregiver and having a cavity defined therein. An identification badge is configured to be positioned within the cavity. The identification badge is removable from the caregiver badge. A transceiver is positioned within the caregiver badge and configured to communicate with a positioning system to identify a location of the caregiver. A battery is positioned within the caregiver badge to power the transceiver.

24 Claims, 4 Drawing Sheets

(56) References Cited

U.S. PATENT DOCUMENTS

| | | |
|---|---|---|
| 4,151,407 A | 4/1979 | McBride et al. |
| 4,216,462 A | 8/1980 | McGrath et al. |
| 4,225,953 A | 9/1980 | Simon et al. |
| 4,275,385 A | 6/1981 | White |
| 4,443,693 A | 4/1984 | Berezowski et al. |
| 4,601,064 A | 7/1986 | Shipley |
| 4,649,385 A | 3/1987 | Aires et al. |
| 4,728,928 A | 3/1988 | Shipley |
| 4,759,022 A | 7/1988 | Akerberg |
| 4,837,568 A | 6/1989 | Snaper |
| 4,906,853 A | 3/1990 | Linwood et al. |
| 4,967,195 A | 10/1990 | Shipley |
| 4,979,217 A | 12/1990 | Shipley |
| 4,990,892 A | 2/1991 | Guest et al. |
| 5,017,794 A | 5/1991 | Linwood et al. |
| 5,027,314 A | 6/1991 | Linwood et al. |
| 5,051,741 A | 9/1991 | Wesby |
| 5,062,151 A | 10/1991 | Shipley |
| 5,119,104 A | 6/1992 | Heller |
| 5,153,584 A | 10/1992 | Engira |
| 5,214,421 A | 5/1993 | Vernon et al. |
| 5,218,344 A | 6/1993 | Ricketts |
| 5,260,840 A | 11/1993 | Hatanaka et al. |
| 5,291,399 A | 3/1994 | Chaco |
| 5,317,309 A | 5/1994 | Vercellotti et al. |
| 5,319,363 A | 6/1994 | Welch et al. |
| 5,341,412 A | 8/1994 | Ramot et al. |
| 5,355,222 A | 10/1994 | Heller et al. |
| 5,363,425 A | 11/1994 | Mufti et al. |
| 5,387,993 A | 2/1995 | Heller et al. |
| 5,390,238 A | 2/1995 | Kirk et al. |
| 5,396,224 A | 3/1995 | Dukes et al. |
| 5,402,469 A | 3/1995 | Hopper et al. |
| 5,412,715 A | 5/1995 | Volpe |
| 5,417,222 A | 5/1995 | Dempsey et al. |
| 5,426,425 A | 6/1995 | Conrad et al. |
| RE35,035 E | 9/1995 | Shipley |
| 5,455,851 A | 10/1995 | Chaco et al. |
| 5,458,123 A | 10/1995 | Unger |
| 5,461,665 A | 10/1995 | Shur et al. |
| 5,465,082 A | 11/1995 | Chaco |
| 5,471,404 A | 11/1995 | Mazer |
| 5,493,283 A | 2/1996 | Hopper et al. |
| 5,500,651 A | 3/1996 | Schuermann |
| 5,515,426 A | 5/1996 | Yacenda et al. |
| 5,534,876 A | 7/1996 | Erickson et al. |
| 5,541,585 A | 7/1996 | Duhame et al. |
| 5,548,637 A | 8/1996 | Heller et al. |
| 5,561,412 A | 10/1996 | Novak et al. |
| 5,572,195 A | 11/1996 | Heller et al. |
| 5,576,952 A | 11/1996 | Stutman et al. |
| 5,588,009 A | 12/1996 | Will |
| 5,594,786 A | 1/1997 | Chaco et al. |
| 5,627,524 A | 5/1997 | Fredrickson et al. |
| 5,633,742 A | 5/1997 | Shipley |
| 5,682,142 A | 10/1997 | Loosmore et al. |
| 5,689,229 A | 11/1997 | Chaco et al. |
| 5,699,038 A | 12/1997 | Ulrich et al. |
| 5,732,711 A | 3/1998 | Fitzpatrick et al. |
| 5,742,233 A | 4/1998 | Hoffman et al. |
| 5,745,037 A | 4/1998 | Guthrie et al. |
| 5,745,272 A | 4/1998 | Shipley |
| 5,793,861 A | 8/1998 | Haigh |
| 5,815,566 A | 9/1998 | Ramot et al. |
| 5,818,617 A | 10/1998 | Shipley |
| 5,822,418 A | 10/1998 | Yacenda et al. |
| 5,822,544 A | 10/1998 | Chaco et al. |
| 5,835,023 A | 11/1998 | Ito et al. |
| 5,838,223 A | 11/1998 | Gallant et al. |
| 5,838,698 A | 11/1998 | Doubler et al. |
| 6,009,333 A | 12/1999 | Chaco |
| 6,104,295 A | 8/2000 | Gaisser et al. |
| 6,133,837 A | 10/2000 | Riley |
| 6,147,592 A | 11/2000 | Ulrich et al. |
| 6,198,394 B1 | 3/2001 | Jacobsen et al. |
| 6,211,790 B1 | 4/2001 | Radomsky et al. |
| 6,252,512 B1 | 6/2001 | Riley |
| 6,259,355 B1 | 7/2001 | Chaco et al. |
| 6,344,794 B1 | 2/2002 | Ulrich et al. |
| 6,362,778 B2 | 3/2002 | Neher |
| 6,848,207 B1 * | 2/2005 | Powell .................... G09F 3/207 224/257 |
| 6,972,683 B2 | 12/2005 | Lestienne et al. |
| 7,301,453 B2 | 11/2007 | Fry |
| 7,774,969 B1 * | 8/2010 | Silverman ............ H05K 5/0278 224/257 |
| 7,825,794 B2 | 11/2010 | Janetis et al. |
| 8,451,120 B2 | 5/2013 | Johnson, Jr. et al. |
| 8,659,429 B1 * | 2/2014 | Wagner ................. G01S 5/0263 340/539.13 |
| 8,823,491 B2 * | 9/2014 | Luke ..................... G08B 21/24 340/539.1 |
| 9,619,989 B1 * | 4/2017 | Ewing .................. G08B 21/245 |
| 9,965,657 B1 | 5/2018 | Amir et al. |
| 2003/0090387 A1 | 5/2003 | Lestienne et al. |
| 2003/0132845 A1 | 7/2003 | McDaniel, III |
| 2006/0220837 A1 * | 10/2006 | Kozlay .................. G07C 9/257 340/539.11 |
| 2007/0205886 A1 * | 9/2007 | Huseth ................... A62B 33/00 340/539.15 |
| 2011/0316695 A1 * | 12/2011 | Li .......................... G01S 11/06 340/539.13 |
| 2015/0310180 A1 * | 10/2015 | Pattekar ................ G16H 40/20 705/2 |
| 2016/0029160 A1 * | 1/2016 | Theurer ................ G01S 5/0284 455/456.1 |
| 2017/0019765 A1 * | 1/2017 | Hoyer ................... H04W 4/021 |

FOREIGN PATENT DOCUMENTS

| | | |
|---|---|---|
| GB | 2 265 038 A | 9/1993 |
| JP | 2-28581 A | 1/1990 |
| JP | 6-186316 A | 7/1994 |
| JP | 10-38603 A | 2/1998 |
| WO | 95/01014 A1 | 1/1995 |
| WO | 99/34341 A1 | 7/1999 |
| WO | 01/33748 A1 | 5/2001 |
| WO | 01/46711 A1 | 6/2001 |

* cited by examiner

CAREGIVER LOCATING TAG HAVING ADVANCED FUNCTIONALITY

The present application claims the benefit, under 35 U.S.C. § 119(e), to U.S. Provisional Patent Application No. 62/775,468, filed Dec. 5, 2018, which is hereby incorporated by reference herein in its entirety.

BACKGROUND

The present disclosure relates to caregiver locating tags or badges, and more particularly to caregiver locating tags or badges having advanced functionality.

Generally, caregiver locating tags or badges are worn by caregivers in a healthcare facility so that other components of a real time locating system (RTLS) can determine the locations of the caregivers within the healthcare facility. The terms "tag(s)" and "badge(s)" are used interchangeably herein. The caregiver locating badge may permit the caregiver to have access to designated areas of the healthcare facility while preventing access to other caregivers who are not authorized to have access to the designated areas. Based on communication with the caregiver locating badge, the RTLS is able to determine that the caregiver has entered a patient's room, for example. Thus, signals from some caregiver badges are used to track the caregiver's whereabouts within a healthcare facility.

Sometimes caregivers are required to wear multiple badges or tags while at work. For example, caregivers may have an employee tag or card with a magnetic strip or other identifying chip and may also have a badge included as part of the RTLS. Having to keep track of multiple badges and tags may introduce inefficiency in the caregiver's work activities if one of the badges becomes lost. Wearing multiple tags on different parts of the caregiver's clothing or body also can be cumbersome since these tend to hang downwardly from the caregiver when the caregiver leans over to attend to a patient, for example.

The work activities of caregivers in healthcare facilities sometimes are interrupted due to having to recharge low batteries of their respective badges. Occasionally, caregiver's may require assistance with a combative or uncooperative patient. Some room stations of nurse call systems have a user input such as a button which is designated for caregivers to call for assistance when under duress. However, in some situations, the caregiver may not be able to reach the room station to place such a call. Accordingly, there is room for improvement in connection with badges used in RTLS's to increase caregiver efficiency and safety.

SUMMARY

The present disclosure includes one or more of the features recited in the appended claims and/or the following features which, alone or in any combination, may comprise patentable subject matter.

In one aspect of the disclosed embodiments, a caregiver badge system includes a caregiver badge configured to be worn by a caregiver and having a cavity defined therein. An identification badge is configured to be positioned within the cavity. The identification badge is removable from the caregiver badge. A transceiver is positioned within the caregiver badge and configured to communicate with a positioning system to identify a location of the caregiver. A battery is positioned within the caregiver badge to power the transceiver.

In some embodiments, the battery may be rechargeable. The battery may be removable from the caregiver badge to recharge. In some embodiments, an indicator may notify the caregiver when the battery is low on charge. In some embodiments, the indicator may be at least one of a visual or audible alert. In some embodiments, the system may include a plurality of batteries. A first battery may be positioned within the caregiver badge to power the transceiver while at least one second battery may be recharged. In some embodiments, a charging station may be provided to charge the at least one second battery.

In some embodiments, a charging station may be provided. The caregiver badge may be configured to couple to the charging station to recharge the battery. In some embodiments, a docking station may be provided. The caregiver badge may be configured to couple to the docking station. The docking station may monitor which caregiver badge is coupled thereto to track which caregivers are off duty. In some embodiments, the docking station may have a battery recharger to recharge the battery when the caregiver badge is coupled thereto.

In some embodiments, a positioning system may track movement of the caregiver badge through communication with the transceiver. The positioning system may identify duress movement of the caregiver and may send a duress signal to a nurse's station. In some embodiments, the duress movement may be at least one of rapid movement and non-linear movement. In some embodiments, a duress button may be positioned on the caregiver badge. The duress button may be configured to be activated by the caregiver during duress. The transceiver may send a duress signal to a nurse's station when the duress button is activated.

In another aspect of the disclosed embodiments, a caregiver tracking system includes a positioning system. A caregiver badge is configured to be worn by a caregiver. The caregiver badge has a transceiver that communicates with the positioning system to identify a location of the caregiver. A duress button is positioned on the caregiver badge. The positioning system tracks movement of the caregiver badge through communication with the transceiver. The positioning system identifies duress movement of the caregiver. A duress signal is transmitted to a nurse's station when at least one of duress movement is detected or the duress button is activated.

In some embodiments, the duress movement may be at least one of rapid movement and non-linear movement. The duress movement may be detected based on signals from a sensor such as an accelerometer including in circuitry of the caregiver badge.

In some embodiments, the caregiver badge may have a cavity defined therein. An identification badge may be configured to be positioned within the cavity. The identification badge may be removable from the casing. In some embodiments, the caregiver badge has a battery to power the transceiver. In some embodiments, the battery may be rechargeable. The battery may be removable from the caregiver badge to recharge. In some embodiments, an indicator may notify the caregiver when the battery is low on charge. In some embodiments, the indicator may be at least one of a visual or audible alert. In some embodiments, a plurality of batteries is provided. A first battery may be positioned within the caregiver badge to power the transceiver while at least one second battery is recharged. In some embodiments, a charging station may charge the at least one second battery. In some embodiments, the caregiver badge may be configured to couple to a charging station to recharge the battery.

In some embodiments, a docking station is provided. The caregiver badge may be configured to couple to the docking station. The docking station may monitor which caregiver badge is coupled thereto to track which caregivers are off duty. In some embodiments, the docking station further may have a battery charger to charge a battery of the caregiver badge.

In yet another aspect of the disclosed embodiments, a caregiver badge system includes a caregiver badge configured to be worn by a caregiver. A transceiver is positioned within the caregiver badge and configured to communicate with a positioning system to identify a location of the caregiver. A battery is positioned within the caregiver badge to power the transceiver. The caregiver badge is configured to couple to a docking station. The docking station monitors which caregiver badge is coupled thereto to track which caregivers are off duty. The docking station includes a battery recharger to recharge the battery when the caregiver badge is coupled thereto.

In some embodiments, the caregiver badge may have a cavity defined therein. An identification badge may be configured to be positioned within the cavity. The identification badge may be removable from the casing, In some embodiments, the caregiver badge may have an indicator to notify the caregiver when the battery is low on charge. In some embodiments, the indicator may be at least one of a visual or audible alert.

In some embodiments, a positioning system may track movement of the caregiver badge through communication with the transceiver. The positioning system may identify duress movement of the caregiver and may send a duress signal to a nurse's station. In some embodiments, the movement may be at least one of rapid movement and non-linear movement. In some embodiments, the caregiver badge further may have a duress button. The duress button may be configured to be activated by the caregiver during duress. The transceiver may send a duress signal to a nurse's station when the duress button is activated.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
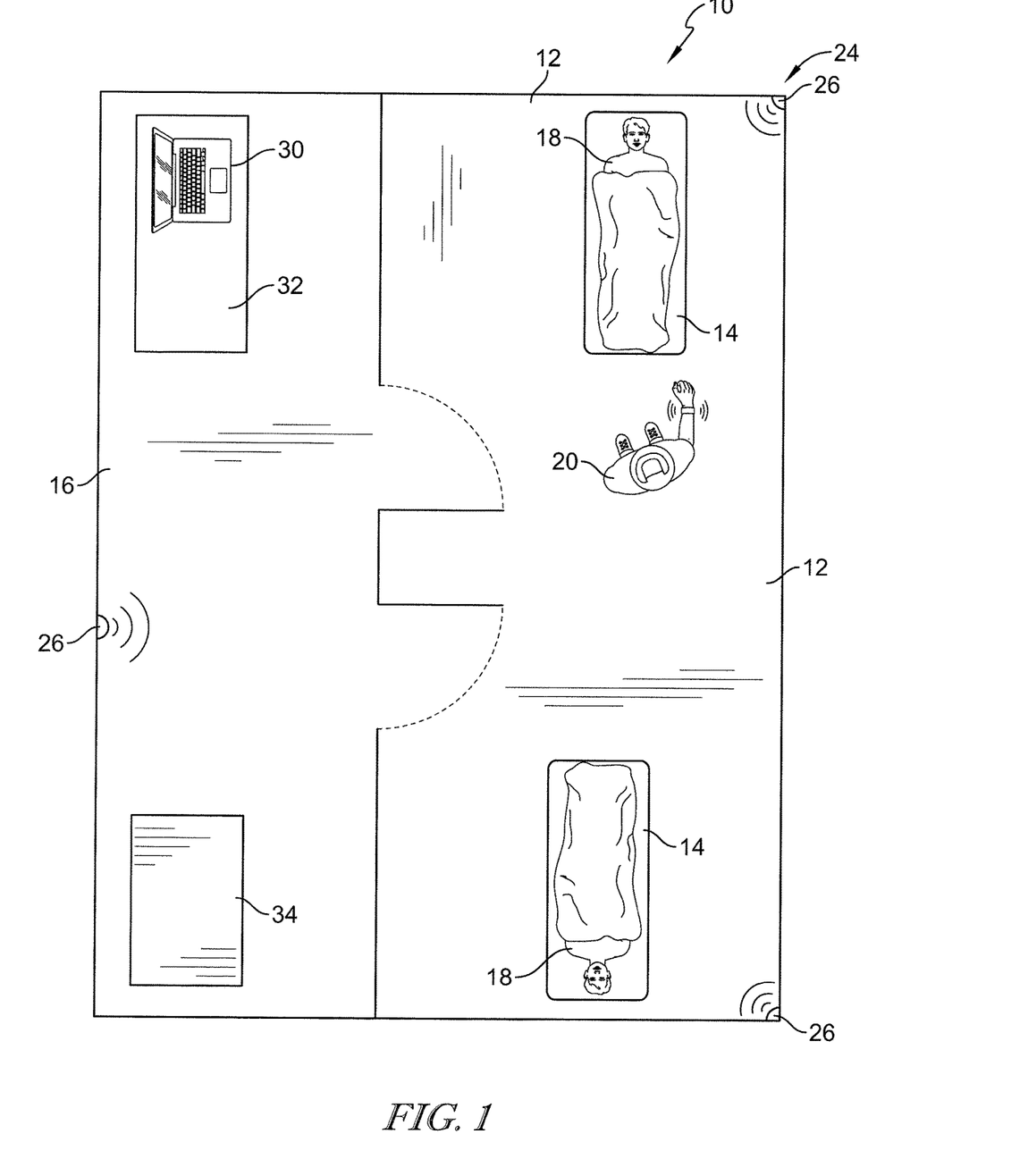
FIG. 1 is a diagrammatic view of a floor plan of part of a healthcare facility showing two patients lying in respective beds in a semi-private room, a caregiver attending to one of the patients, the caregiver having a locating badge configured as a wrist band, a set of locating transceivers of a real time locating system (RTLS) that receive wireless signals from the locating badge, a computer at a nurse's station in a hallway adjacent the patient room, and a security station also located in the hallway.

Referring to FIG. 1, a health care facility 10 includes a plurality of patient rooms 12. In the illustrative embodiment, two patients are shown in a semi-private room 12; however, it is known for healthcare facilities to have any number of patient rooms 12, including single-patient or private rooms. The patient rooms 12 include a patient support apparatus 14. The patient support apparatus 14 is illustrated as a bed; however, the patient support apparatus 14 may take the form of any apparatus for supporting a patient, e.g. a bench, a couch, a chair, a stretcher, and the like. The patient support apparatus 14 supports a patient 18 thereon. FIG. 1 also illustrates a caregiver 20, who may enter the patient room 12 to assess the patient 18. For example, the caregiver 20 may enter the room 12 to acquire clinical inputs related to the patient, e.g. acquire vital signs. The caregiver 20 may also enter the patient room 12 to dispense medication to the patient 18 or otherwise check on the patient 18.

A positioning system 24 is provided within the patient rooms 12. The positioning system 24 may be embodied as an ultra-wideband positioning system. The positioning system includes a plurality of locating transceivers 26 positioned throughout the patient rooms 12 and the hallways 16 of the healthcare facility 10. In some embodiments, the transceivers 26 transmit signals throughout the patient room 12. The signals are received by a caregiver badge 28 that is coupled to the caregiver 20, e.g. worn around the caregiver's neck, attached to the caregiver's clothes such as with a clip, etc. The caregiver badge 28 receives the signals from the transceivers 26 and, in response, transmits a return signal to at least one of the transceivers 26. In some embodiments, by triangulating a plurality of signals from the transceivers 26 and the return signal from the caregiver badge 28, a position of the caregiver badge 28 may be determined. That is, the positioning system 24 can determine whether the caregiver 20 is in a patient room 12, the hallway 16, etc. The positioning system 24 may include additional components such as hub computers, gateways, servers, and the like (not shown) that receive signals from transceivers 26 and that store locations of caregivers 20 in a locating database. The database of caregiver locations is accessible for viewing on a location module or computer 30. Thus, the server of the locating system 24 transmits information indicative of the location of the caregiver badges 28, and therefore the corresponding caregivers, to computer 30 for display. The location module 30 may be positioned in the hallway 16 or any other centralized location, for example at a nurse's station 32. Accordingly, a position of the caregiver 20 can be monitored, for example at the nurse's station 32 or any other centralized location.

The positioning system 24, therefore, tracks substantially real-time movement of the caregivers 20 throughout the healthcare facility. Accordingly illustrative positioning system 24 is a real time locating system (RTLS) according to the present disclosure. Thus, the positioning system 24 can track the movement of the caregiver 20 between patient rooms 12 and between the hallway 16 and patient rooms 12. In some embodiments, the positioning system 24 can also monitor caregiver movement within the healthcare facility. For example, the positioning system 24 can determine whether the caregiver 20 is moving erratically. Erratic movement may include non-linear movement, e.g. zigzagging. The positioning system 24 can also monitor a rate at which the caregiver 20 is moving through the healthcare facility 10. The course of the caregiver 20 and a rate of the caregiver's movement is transmitted to the location module 30. The location module 30 monitors such movement and rate of movement to determine whether the caregiver 20 may be in distress. For example, if the caregiver 20 is moving at a rate of speed that exceeds a threshold speed, such as if the caregiver is running, the location module 30 may provide an alert at the nurse's station. Likewise, if the course of the caregiver's movement is outside a threshold of normal linear movement, the location module may give a similar alert. The alert may be in the form of a visual or audible alarm at the nurse's station 32 or at a security station 34. Such monitoring of caregiver movement may be implemented at any location throughout the healthcare facility, for example, in a psychiatric ward, emergency room, or any other suitable location where a caregiver 20 may be in danger.

Figure 2:
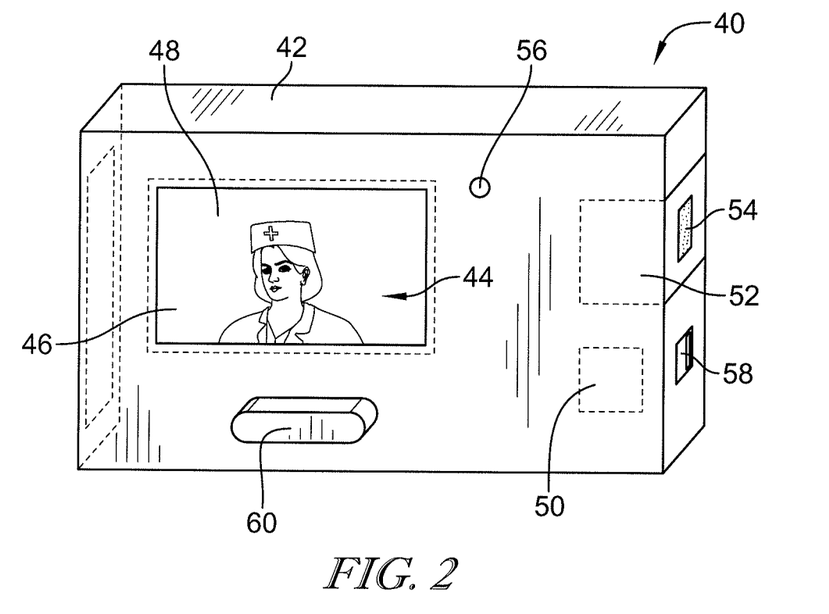
FIG. 2 is a perspective view of an embodiment of a caregiver badge according to the present disclosure showing a duress button situated beneath a photo of the caregiver that is included as part of an identification (ID) tag that is inserted into a cavity defined by a transparent cover of the caregiver badge so that the caregiver badge and ID tag are transported and worn together as a single unit.

Referring to FIG. 2, an embodiment of a caregiver badge 40 is illustrated. While the caregiver badge 40 has the function of communicating with the positioning system 24, it should be noted that the caregiver badge 40 may have additional functionality that enables the caregiver 20 to access areas of the healthcare facility 10. For example, the caregiver badge 40 may permit access to medication.

The caregiver badge 40 includes an outer casing 42 that may be formed from plastic or the like. The outer casing 42 is generally durable and waterproof to protect circuitry within the outer casing 42. Such an outer casing allows for easy cleaning and infection control, for example. A cavity 44 is formed within the caregiver badge 40 and is configured to receive and retain an identification (ID) badge or tag 46 therein. Thus, cavity 44 is configured as a pocket with an open edge in some embodiments. Accordingly, the caregiver 20 can carry or wear both ID tag 46 and caregiver badge 40 together as a single unit. A clear cover 48 retains the identification badge 46 within the cavity 44. The cover 48 is configured as an outer pocket panel or is openable so that the identification badge 46 can be removed from cavity 44. For example, the caregiver 20 can insert their identification badge 46 into cavity 44 of any caregiver badge 40 at the beginning of a shift and remove the identification badge 46 after the shift so that the caregiver badge 40 may be used by other caregivers 20 on subsequent shifts.

A transceiver 50 is positioned within the outer casing 42. The transceiver 50 is configured to communicate with the transceivers 26 of positioning system 24. That is, the transceiver 50 receives signals from and sends signals to the various transceivers 26. A battery 52 is positioned within the outer casing 42 to power the transceiver 36 and other circuitry included within badge 40. In some embodiments, the battery 52 is replaceable. In some embodiments, the battery 52 is rechargeable. The battery 52 includes an electric connector 54 that is configured to attach to a charging station (described in more detail below). A low battery indicator 56 is provided within the outer casing 42 and is viewable on the outer casing 42. The low battery indicator 56 may be a light (e.g., light emitting diode (LED)) to provide a visual indication that the battery 52 is low or a speaker or buzzer to provide an audible indication that the battery 52 is low. In some embodiments, the caregiver badge 40 may include both a light and a speaker (or buzzer) for the low battery indicator 56. In such an embodiment, the caregiver 20 may be able to select the type of low battery indication that he/she desires. In other embodiments, the visual indicator indicates a charge level of the battery 52 such as by having a series of LED's that are turned on or off depending upon the charge level (e.g., all on for full charge, half on for half charge, all off for no charge). A data connector 58 is also provided on casing 42 to couple the caregiver badge 40 to a docking station (described in more detail below). It should be noted that other circuitry (not shown) known in the art may be positioned within the outer casing to provide functionality to the caregiver badge 40.

A duress button 60 is positioned on the caregiver badge 40. The duress button 60 is operable to send a signal to the location module 30 indicating that the caregiver 20 is in duress. In response to the duress button 60 being pressed, the circuitry within badge 40 emits a wireless duress signal. The duress signal is ultimately communicated to the location module 30 at the nurse's station 32 and/or the security station 34 to provide a notification that the caregiver 20 is in duress. In some embodiments, use of the duress button 60 results in a duress notification being sent to the positioning system 24 that tracks the caregiver 20 movement in lieu of or in addition to being sent to station 32 and/or station 34. In some embodiments, badge 40 includes an accelerometer as part of its circuitry. The accelerometer senses the caregiver's movement while wearing the badge 40. Accordingly, if the caregiver 20 is unable to activate the duress button 60 but is moving erratically due to attempting to control a combative or uncooperative patient, for example, the positioning system 24 is able to detect the erratic movement of the caregiver 20 and sends an associated duress signal to the nurse's station 32 and/or the security station 34.

Figure 3:
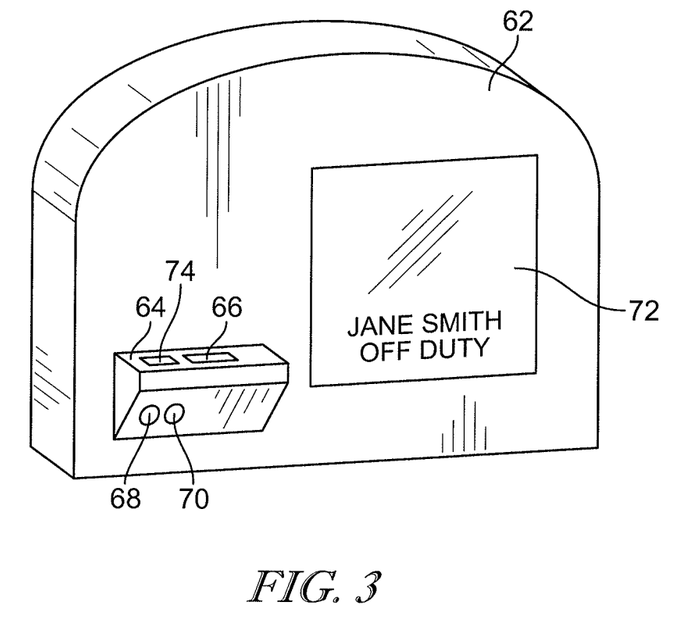
FIG. 3 is a perspective view of an embodiment of a docking station that may be used with the caregiver badge shown in FIG. 2, the docking station having a port to receive a caregiver badge for recharging and a display screen to indicate that a caregiver is off duty when the caregiver's badge is coupled to the port.

Referring to FIG. 3, a docking station 62 is configured to receive the caregiver badge 40. The docking station 62 includes a docking area 64 wherein the caregiver badge 40 is positioned and retained. Although only one docking area 64 is illustrated, it will be appreciated by one of skill in the art that the docking station 62 can have a plurality of docking areas 64 to retain a plurality of caregiver badges 40. An electrical connector or port 66 is positioned within the docking area 64. The electrical connector 66 corresponds to and mates with the electrical connector 54 of the battery 52 of the caregiver badge 40. In some embodiments, the electrical connector 66 includes a male connector and the electrical connector 54 includes a female connector to receive the electrical connector 66. In other embodiments, the electrical connector 54 includes a male connector and the electrical connector 66 includes a female connector to receive the electrical connector 54. The battery 52 electrically couples to the docking station 62 when the caregiver badge 40 is positioned within the docking area 64 so that the docking station 62 can recharge the battery 52 of the caregiver badge 40. In some embodiments, the battery 52 is removed from the caregiver badge 40 and coupled to the docking station 62 without the remainder of caregiver badge 40. After charging, the battery 52 can be reattached to the caregiver badge 40. A "charging" indicator 68, for example a light, indicates that the battery 52 is charging. A "charged" indicator 70, for example a light, indicates that the battery 52 is fully charged.

The docking station 62 may also be used to track which caregivers 20 are on duty, and which caregivers 20 are off duty, e.g. at lunch, day off, etc. through a data connector 74. The data connector 74 corresponds to and mates with the data connector 58 of the caregiver badge 40. In some embodiments, the data connector 74 includes a male connector and the data connector 58 includes a female connector to receive the data connector 74. In other embodiments, the data connector 58 includes a male connector and the data connector 74 includes a female connector to receive the data connector 58. The caregiver badge 40 may be assigned to a specific caregiver 20. Each caregiver 20 docks his/her caregiver badge 40 when he/she is off duty. In an embodiment, having a plurality of docking areas 64, a plurality of caregiver badges 40 may be docked while multiple caregivers 20 are off duty. When a caregiver 20 docks his/her caregiver badge 40, the docking station 62 indicates that the respective caregiver 20 is off duty. A screen 72 is provided on the docking station 62 to display the names of caregivers 20 who are off duty. Alternatively or additionally, the screen 72 displays the names of caregivers who are on duty by detecting that the respective caregiver badge 40 is not docked. In some embodiments, the docking station 62 is electronically coupled to a monitor or other electronic device, e.g. computer, tablet, phone, etc., such as computer 30, and sends data to the device to display a list of caregivers 20 who are on duty and/or off duty.

Figure 4:
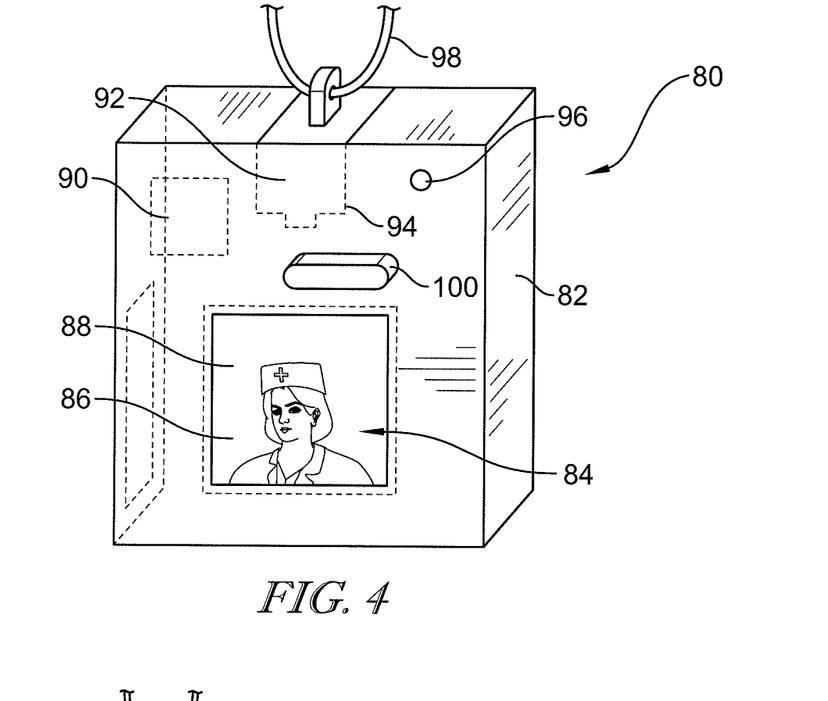
FIG. 4 is a perspective view of another embodiment of a caregiver badge coupled to a lanyard that may be worn around a caregiver's neck, the lanyard being coupled to a battery that is quickly detachable from a main body of the caregiver badge so that a new battery with a new lanyard can be quickly attached to the main body.

Referring to FIG. 4, another embodiment of a caregiver badge 80 is illustrated. While the caregiver badge 80 has the function of communicating with the positioning system 24, it should be noted that the caregiver badge 80 may have additional functionality that enables the caregiver 20 to access areas of the healthcare facility 10. For example, the caregiver badge 80 may permit access to medication.

The caregiver badge 80 includes an outer casing 82 that may be formed from plastic or the like. The outer casing 82 is generally durable and waterproof to protect circuitry within the outer casing 82. Such an outer casing allows for easy cleaning and infection control, for example. A cavity 84 is formed within the caregiver badge 80 and is configured to retain an identification (ID) badge or tag 86 therein. Thus, cavity 84 is configured as a pocket with an open edge in some embodiments. Accordingly, the caregiver 20 can carry or wear both ID tag 86 and caregiver badge 80 together as a single unit. A clear cover 88 retains the identification badge 86 within the cavity 84. The cover 88 is configured as an outer pocket panel or is openable so that the identification badge 86 can be removed from cavity 84. For example, the caregiver 20 can insert their identification badge 86 into cavity 84 of any caregiver badge 80 at the beginning of a shift and remove the identification badge 86 after the shift so that the caregiver badge 80 may be used by other caregivers 20 on subsequent shifts.

A transceiver 90 is positioned within the outer casing 82. The transceiver 90 is configured to communicate with the transceivers 26 of positioning system 24. That is, the transceiver 90 receives signals from and sends signals to the various transceivers 26. A battery 92 is positioned within the outer casing 82 to power the transceiver 90 and other circuitry included within badge 80. In some embodiments, the battery 92 is replaceable. In some embodiments, the battery 92 is rechargeable. The battery 92 includes an electric connector 94 that is plugged into the caregiver badge 80. A low battery indicator 96 is provided within the outer casing 82 and is viewable on the outer casing 82. The low battery indicator 96 may be a light (e.g., light emitting diode (LED)) to provide a visual indication that the battery 92 is low or a speaker or buzzer to provide an audible indication that the battery 92 is low. In some embodiments, the caregiver badge 80 may include both a light and a speaker (or buzeer) for the low battery indicator 96. In such an embodiment, the caregiver 20 may be able to select the type of low battery indication that he/she desires. In other embodiments, the visual indicator indicates a charge level of the battery 92 such as by having a series of LED's that are turned on or off depending upon the charge level (e.g., all on for full charge, half on for half charge, all off for no charge). The battery 92 is coupled to a lanyard 98 in the illustrative example but may be coupled to a clip or other coupler in other embodiments.

The battery 92 is manually removable from the main body of caregiver badge 80 such that the battery 92 remains on the lanyard 98 to avoid losing the battery 92. It should be noted that other circuitry (not shown) known in the art may be positioned within the outer casing to provide functionality to the caregiver badge 40. A new battery is then manually attachable to the main body of caregiver badge 80. Thus, an existing battery 92 is quickly and easily replaced manually with new a new battery 92 when the existing battery becomes low on charge. The batteries 92 slide into and out of electrical connector 94 without the need to remove any access panels on the outer casing 82. This is an advantage over prior art locating badges having access panels that must first be removed, sometimes with tools such as screwdrivers, before access to the battery can be achieved. Casing 82 and/or batteries 92 may include snap fingers or ribs or detents, as the case may be, to help retain batteries 92 relative to casing 82 but that still permit manual removal of the batteries 92 from casing 82.

A duress button 100 is positioned on the caregiver badge 80. The duress button 100 is operable to send a signal to the location module 30 indicating that the caregiver 20 is in duress. In response to the duress button 100 being pressed, the circuitry within badge 80 emits a wireless duress signal. The duress signal is ultimately communicated to the location module 30 at the nurse's station and/or the security station to provide a notification that the caregiver 20 is in duress. In some embodiments, use of the duress button 100 results in a duress notification being sent to the positioning system 24 that tracks the caregiver 20 movement in lieu of or in addition to being sent to station 32 and/or station 34. In some embodiments, badge 80 includes an accelerometer as part of its circuitry. The accelerometer senses the caregiver's movement while wearing the badge 40. Accordingly, if the caregiver 20 is unable to activate the duress button 100 but is moving erratically due to attempting to control a combative or uncooperative patient, for example, the positioning system 24 is able to detect the erratic movement of the caregiver 20 and sends an associated duress signal to the nurse's station 32 and/or the security station 34.

Figure 5:
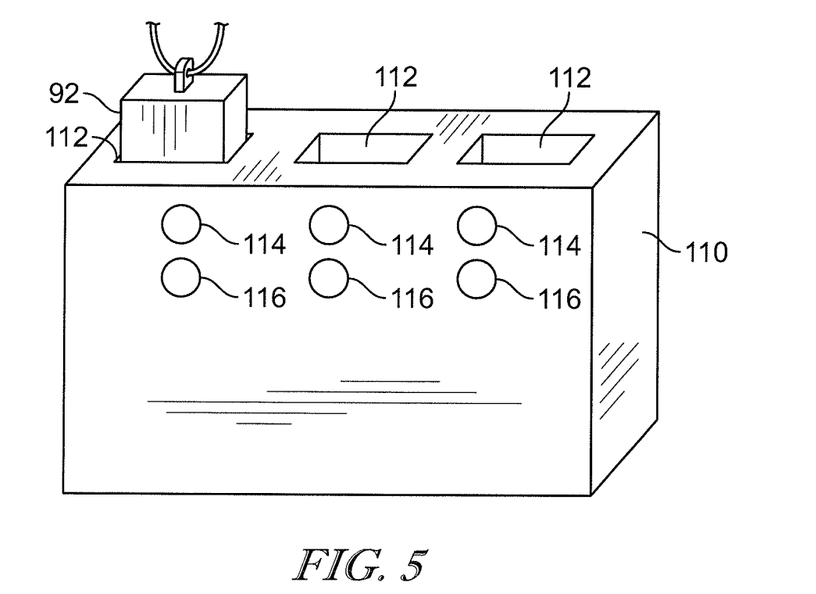
FIG. 5 is a perspective view of an embodiment of a charging station that may be used to simultaneously recharge multiple caregiver badges like the caregiver badge shown in FIG. 4.

Referring to FIG. 5, a charging station 110 includes a plurality of electrical ports or connectors 112 that are configured to receive the electrical connector 94 of battery 92. The battery 92 is removable from the caregiver badge 80 and attachable to the charging station 110 to charge the battery 92. In some embodiments, the electrical connector 94 is a male connector and the electrical connector 112 is a female connector configured to receive the electrical connector 94. In some embodiments, the electrical connector 112 is male connector and the electrical connector 94 is a female connector configured to receive the electrical connector 112. Although FIG. 5 illustrates three electrical connectors 112, it will be appreciated that the charging station 110 may have any number of suitable electrical connectors 112. A "charging" indicator 114, for example a light, indicates that the battery 92 is charging. A "charged" indicator 116, for example a light, indicates that the battery 92 is fully charged. Thus, when a caregiver needs to replace an existing, depleted battery 92 of badge 80, the caregiver can go to charging station 110 and pull out a fully charged battery 92 from one of ports 112 and swap it out with the depleted battery 92. The depleted battery 92 is then inserted into one of ports 112 of charging station 110 for recharging.

Figure 6:
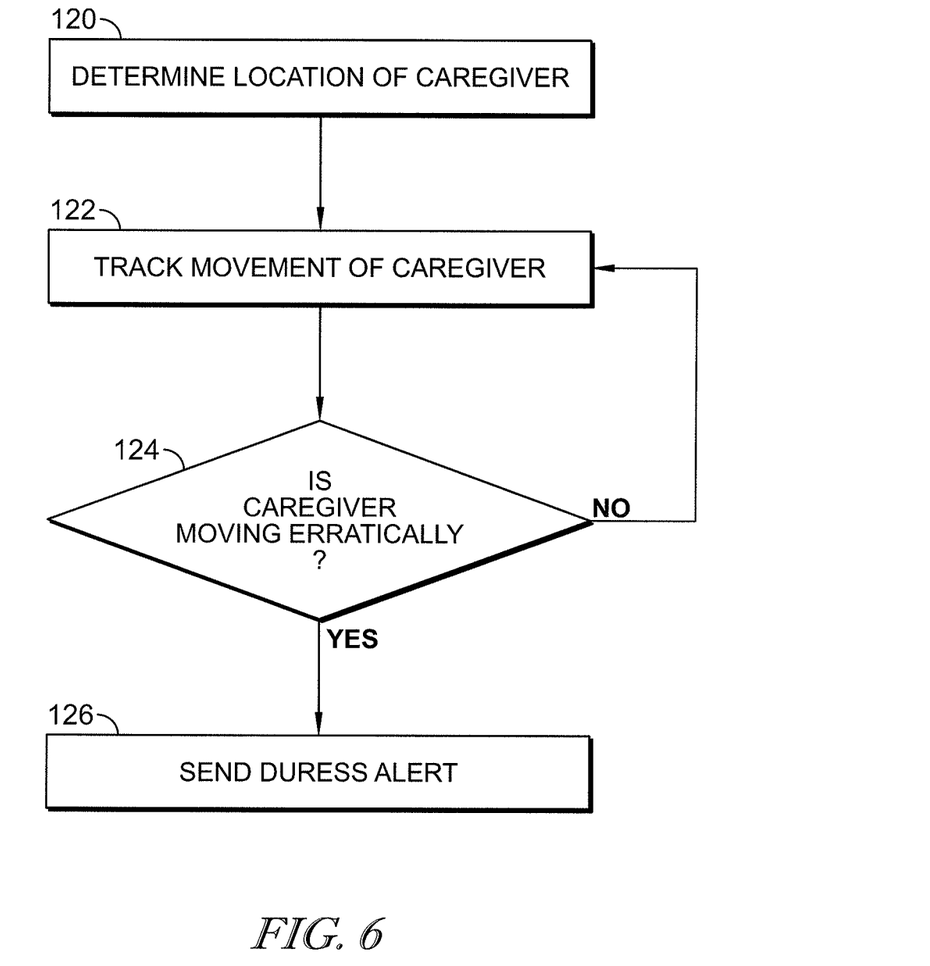
FIG. 6 is a flowchart of a method of tracking movement of a caregiver so that a duress alert can be sent if the caregiver is moving erratically.

Referring to FIG. 6, a method is shown in which a computer of the positioning system 24, such as a locating server or computer 30, determines a location of the caregiver 20, at step 120. Thereafter, at step 122, the positioning system 24 tracks the movement of the caregiver 20. For example, the positioning system 24 tracks a course or route of the caregiver's movement and/or tracks a rate of speed of the caregiver's movement. The server of locating system 24 or location module 30 then determines whether the course of the caregiver's movement or the rate of speed is indicative of erratic movement, at step 124. If the movement is not erratic, the positioning system 24 continues to monitor the movement of the caregiver 20, at step 122. If the movement is erratic, the location module 30 displays a duress alert at the nurse's station 32 and/or at the security station 34, at step 126. Other caregivers at stations 32 and/or station 34 can then response to the duress alert and assist the caregiver that is believed to be under duress.

Examples of circuitry included in locating tags or badges, as well as further details of RTLS's, can be found, for example, in U.S. Pat. Nos. 9,965,657; 6,972,693; 6,104,295; 5,633,742; and 5,561,412 (see FIGS. 4 and 5 and the related description), each of which is incorporated by reference herein in its entirety to the extent not inconsistent with the present disclosure which shall control as to any inconsistencies.

Although this disclosure refers to specific embodiments, it will be understood by those skilled in the art that various changes in form and detail may be made without departing from the subject matter set forth in the accompanying claims.

The invention claimed is:

1. A caregiver badge system for use with a real time locating system (RTLS) of a healthcare facility that is operable to determine movements of caregivers in the healthcare facility, each caregiver having an employee identification tag, the caregiver badge system including a caregiver badge comprising:
a housing having a cavity that is sized and configured to receive the employee identification tag therein,
a coupler attached to the housing and configured to permit the housing to be worn by the caregiver;
badge circuitry positioned within the housing and configured to communicate wirelessly with fixed transceivers of the RTLS which triangulates a plurality of signals from the fixed transceivers to identify a location of the caregiver,
a duress button positioned on the housing and being activatable to send a first duress signal to a nurse's station, and
a battery positioned within the housing to power the badge circuitry,
wherein the badge circuitry identifies duress movement of the caregiver without the duress button being activated resulting in a second duress signal being transmitted to the nurse's station when the duress movement is detected,
wherein the duress movement comprises at least one of rapid movement and non-linear movement.

2. The caregiver badge system of claim 1, wherein the battery is rechargeable, the battery being removable from the housing to recharge.

3. The caregiver badge system of claim 2, further comprising an indicator to notify the caregiver when the battery is low on charge.

4. The caregiver badge system of claim 3, wherein the indicator comprises at least one of a visual or audible alert.

5. The caregiver badge system of claim 2, further comprising a plurality of batteries, wherein a first battery is positioned within the housing to power the badge circuitry while at least one second battery is recharged.

6. The caregiver badge system of claim 5, further comprising a charging station to charge the at least one second battery.

7. The caregiver badge system of claim 1, further comprising a charging station, the caregiver badge configured to couple to the charging station to recharge the battery.

8. The caregiver badge system of claim 1, further comprising a docking station, the caregiver badge configured to couple to the docking station, the docking station monitoring which caregiver badge is coupled thereto to track which caregivers are off duty.

9. The caregiver badge system of claim 8, wherein the docking station further comprises a battery recharger to recharge the battery when the caregiver badge is coupled thereto.

10. A caregiver tracking system comprising:
a positioning system,
a caregiver badge configured to be worn by a caregiver, the caregiver badge having a transceiver that communicates with fixed transceivers of the positioning system which triangulates a plurality of signals from the fixed transceivers to identify a movement of the caregiver, and
a duress button positioned on the caregiver badge and being activatable to send a first duress signal to a nurse's station,
wherein the positioning system tracks movement of the caregiver badge through communication with the transceiver, wherein the caregiver badge identifies duress movement of the caregiver without the duress button being activated, a second duress signal is transmitted to the nurse's station when the duress movement is detected,
wherein the duress movement comprises at least one of rapid movement and non-linear movement.

11. The caregiver tracking system of claim 10, wherein the caregiver badge further comprises a cavity defined therein and an identification badge configured to be positioned within the cavity, the identification badge being removable from the casing.

12. The caregiver tracking system of claim 10, wherein the caregiver badge further comprises a battery to power the transceiver.

13. The caregiver tracking system of claim 12, wherein the battery is rechargeable, the battery being removable from the caregiver badge to recharge.

14. The caregiver tracking system of claim 12, further comprising an indicator to notify the caregiver when the battery is low on charge.

15. The caregiver tracking system of claim 14, wherein the indicator comprises at least one of a visual or audible alert.

16. The caregiver tracking system of claim 12, further comprising a plurality of batteries, wherein a first battery is positioned within the caregiver badge to power the transceiver while at least one second battery is recharged.

17. The caregiver tracking system of claim 16, further comprising a charging station to charge the at least one second battery.

18. The caregiver tracking system of claim 12, further comprising a charging station, the caregiver badge configured to couple to the charging station to recharge the battery.

19. The caregiver tracking system of claim 10, further comprising a docking station, the caregiver badge configured to couple to the docking station, the docking station monitoring which caregiver badge is coupled thereto to track which caregivers are off duty.

20. The caregiver tracking system of claim 19, wherein the docking station further comprises a battery charger to charge a battery of the caregiver badge.

21. A caregiver badge system comprising:
a caregiver badge configured to be worn by a caregiver,
a transceiver positioned within the caregiver badge and configured to communicate with fixed transceivers of a positioning system which triangulates a plurality of signals from the fixed transceivers to identify a movement of the caregiver,
a battery positioned within the caregiver badge to power the transceiver,
a duress button positioned on the caregiver badge and being activatable to send a first duress signal to a nurse's station, and
a docking station, the caregiver badge configured to couple to the docking station, the docking station monitoring which caregiver badge is coupled thereto to track which caregivers are off duty, the docking station comprising a battery recharger to recharge the battery when the caregiver badge is coupled thereto,
wherein the caregiver badge identifies duress movement of the caregiver without the duress button being activated resulting in a second duress signal being transmitted to the nurse's station when the duress movement is detected,
wherein the duress movement comprises at least one of rapid movement and non-linear movement.

22. The caregiver badge system of claim 21, wherein the caregiver badge comprises:
a cavity defined therein, and
an identification badge configured to be positioned within the cavity, the identification badge being removable from the casing.

23. The caregiver badge system of claim 21, wherein the caregiver badge comprises an indicator to notify the caregiver when the battery is low on charge.

24. The caregiver badge system of claim 23, wherein the indicator comprises at least one of a visual or audible alert.

* * * * *